United States Patent [19]

Breitenbach et al.

[11] Patent Number: 5,846,524

[45] Date of Patent: Dec. 8, 1998

[54] SULFONATE-BEARING POLYAMIDES AND THEIR USE IN HAIRSETTING COMPOSITIONS

[75] Inventors: Jörg Breitenbach, Mannheim; Herbert Fisch, Wachenheim; Stefan Stein, Limburgerhof; Axel Sanner, Frankenthal; Karin Sperling-Vietmeier, Neustadt, all of Germany

[73] Assignee: BASF Aktiengesellschaft, Ludwigshafen, Germany

[21] Appl. No.: 845,281

[22] Filed: Apr. 21, 1997

Related U.S. Application Data

[63] Continuation of Ser. No. 510,538, Aug. 2, 1995, abandoned.

[30] Foreign Application Priority Data

Aug. 8, 1994 [DE] Germany .......................... 44 28 003.3

[51] Int. Cl.$^6$ ...................................................... A61K 7/06
[52] U.S. Cl. ........................ 424/70.17; 528/321; 524/845
[58] Field of Search ........................ 424/70.17; 528/321; 524/845

[56] References Cited

U.S. PATENT DOCUMENTS

| | | | |
|---|---|---|---|
| 3,296,204 | 1/1967 | Caldwell | 260/49 |
| 3,846,507 | 11/1974 | Thomm et al. | 260/857 TW |
| 3,898,200 | 8/1975 | Lofquist | 528/319 |
| 4,374,641 | 2/1983 | Burlone | 8/557 |
| 4,824,916 | 4/1989 | Kershner et al. | 525/420 |
| 4,842,849 | 6/1989 | Grollier et al. | 424/70 |
| 5,102,660 | 4/1992 | Forestier et al. | 424/70.17 |
| 5,137,715 | 8/1992 | Hoshowski et al. | 424/70 |
| 5,158,762 | 10/1992 | Pierce | 424/47 |

*Primary Examiner*—Margaret W. Glass
*Attorney, Agent, or Firm*—Keil & Weinkauf

[57] ABSTRACT

The use of sulfonate-bearing polyamides which are obtainable from $A_1$) from 20 to 99 mol % of a monoaminocarboxylic acid having 2 to 12 C atoms or its lactam, $A_2$) from 0.5 to 40 mol % of a diamine having 2 to 18 C atoms, $A_3$) from 0.5 to 25 mol % of a sulfonate-bearing dicarboxylic acid having 4 to 12 C atoms, and $A_4$) from 0 to 35 mol % of a further dicarboxylic acid having 2 to 16 C atoms, as film-forming agents in hairsetting compositions is described.

5 Claims, No Drawings

SULFONATE-BEARING POLYAMIDES AND THEIR USE IN HAIRSETTING COMPOSITIONS

This application is a continuation of application Ser. No. 08/510,538, filed on Aug. 2, 1995, now abandoned.

The present invention relates to the use of sulfonate-bearing polyamides which are obtainable from $A_1$) from 20 to 99 mol % of a monoaminocarboxylic acid having 2 to 12 C atoms or its lactam, $A_2$) from 0.5 to 40 mol % of a diamine having 2 to 18 C atoms, $A_3$) from 0.5 to 25 mol % of a sulfonate-bearing dicarboxylic acid having 4 to 12 C atoms, and $A_4$) from 0 to 35 mol % of a further dicarboxylic acid having 2 to 16 C atoms, as film-forming agents in hairsetting compositions.

The invention furthermore relates to novel sulfonate-bearing polyamides, their dispersions and hair cosmetic preparations.

Synthetic polymers are in general used for setting, improving the structure of and shaping hair. The polymers which have proven suitable are, for example, those based on vinylpyrrolidone and vinyl acetate, which are customarily applied in the form of alcoholic or aqueous-alcoholic solutions.

The solutions of these materials surround the treated hair with a film which, depending on the type of polymer employed, can have a setting, structure-improving, shaping, luster-improving, smoothing and antistatic effect. The film formed on the hair should on the one hand be moisture-resistant, ie. the hair should not stick and lose its shape even at high atmospheric humidity and on the other hand these films should be able to be washed out easily with an aqueous surfactant solution when cleaning the hair.

On account of the continuously growing demand for more environ-mentally tolerable ingredients, the content of volatile organic constituents (volatile organic compounds—VOC) should be kept as low as possible or reduced even in cosmetic preparations such as, for example, hairspray. This means that the alcohol should increasingly be replaced by water as a solvent.

When using conventional hairsetting polymers, however, this can cause difficulties, as the viscosity and spray behavior of the hairsetting composition and the drying of the polymer films are unsatisfactory at higher water contents.

U.S. Pat. No. 3,296,204 discloses the preparation of sulfonate-containing polyamides by condensation of sulfonated aromatic dicarboxylic acids, whose sulfonic acid is present as an alkali metal salt, with diamines.

DE-C 23 08 266 describes the use of such sulfonated polyamides for the preparation of polyamide yarns.

U.S. Pat. No. 5,158,762 relates to aqueous hairspray compositions in which polymer blends of a water-soluble polymer and a sulfonate-containing polyester or polyester amide are employed as film-forming agents.

It is an object of the present invention to find polymers for use as film-forming agents in hairsetting compositions, which make possible increased proportions of water in the corresponding cosmetic preparations without causing an increase in viscosity or adversely affecting other application properties such as the spray behavior. After application to the hair, non-sticking, clear films with good setting action and good washability should additionally be obtained.

We have now found that this object is achieved by the use of the sulfonate-bearing polyamides, novel polyamides, their dispersions and hair cosmetic preparations, containing sulfonate-bearing polyamides, defined at the outset.

According to the invention, suitable film-forming agents are sulfonate-bearing polyamides which are obtainable from $A_1$) from 20 to 99 mol %, preferably from 30 to 94 mol %, of a monoaminocarboxylic acid having 2 to 12 C atoms or its lactams or mixtures thereof, $A_2$) from 0.5 to 40 mol %, preferably from 7 to 35 mol %, of a diamine having 2 to 18 C atoms, $A_3$) from 0.5 to 25 mol %, preferably from 2.6 to 20 mol %, particularly preferably from 10 to 19 mol %, of a sulfonate-bearing dicarboxylic acid having 4 to 12 C atoms, and $A_4$) 0 to 35 mol %, preferably from 5 to 30 mol %, of a further dicarboxylic acid having 2 to 16 C atoms, where the sum of the molar proportions of the monomers $A_3$) and $A_4$) corresponds to the molar,proportion of the monomer $A_2$).

Suitable monomers $A_1$) for the preparation of polyamides are known monoaminocarboxylic acids or their lactams such as, for example, ω-aminoundecanoic acid, ε-caprolactam, laurolactam, caprylolactam or oenantholactam.

Suitable monomers $A_2$) are aliphatic, cycloaliphatic or aromatic diamines. Suitable diamines are, for example, alkylenediamines or cycloalkyldiamines such as 1,5-pentanediamine, 4,4'-diaminodicyclohexylmethane, 2,2'-(4,4'-diaminodicyclohexyl) propane, 3,3,'-dimethyl-4,4,'-diaminodicyclohexylmethane or, preferably, hexamethylenediamine. Furthermore, piperazine, 2,2,4-trimethylhexamethylenediamine, 2-butyl-2-ethyl-1,5-pentanediamine or 4,7-dioxadecane-1,10-diamine are also suitable.

Suitable sulfonate-bearing monomers $A_3$) are those compounds in which the sulfonate group is present as the lithium, sodium, potassium or ammonium salt. Suitable sulfonate-bearing monomers are salts of aliphatic or aromatic dicarboxylic acids such as, for example, sulfosuccinic acid or 5-sulfopropoxyisophthalic acid.

The sodium salt of 5-sulfoisophthalic acid is preferably employed.

Suitable monomers $A_4$) are, for example, aliphatic dicarboxylic acids such as sebacic acid, azelaic acid, dodecanedicarboxylic acid or preferably adipic acid or sebacic acid. Suitable aromatic dicarboxylic acids are, for example, isophthalic acid or terephthalic acid, which can also be substituted, such as, for example, 3-tert-butylisophthalic acid, furthermore 3,3'- or 4,4'-diphenyldicarboxylic acid, 3,3'- or 4,4'-diphenylmethanedicarboxylic acid, 3,3'- or 4,4'-diphenylsulfonedicarboxylic acid, 1,4- or 2,6-naphthalenedicarboxylic acid or 2-phenoxyterephthalic acid.

Of course, it applies for all monomer groups that mixtures of the particular monomers can also be employed.

Novel polyamides are, according to the invention, those which are obtainable from $a_1$) from 30 to 94.8, preferably from 52 to 85, mol %, in particular from 60 to 80 mol %, of the monomers $A_1$), $a_2$) from 2.6 to 37, preferably from 5.9 to 35.5, mol %, of the monomers $A_2$), $a_3$) from 2.6 to 7, preferably from 2.9 to 6.5, mol % of the monomers $A_3$) and $a_4$) from 0 to 30, preferably from 3 to 29, mol %, in particular from 3 to 25 mol %, of the monomers $A_4$).

The sulfonate-bearing polyamides can be prepared in a manner known per se.

A preferred procedure which may be mentioned is the batch process (batchwise procedure). In this process, the aqueous monomer solution is heated in an autoclave to from 240° to 300° C. in the course of from 0.5 to 3 h, a pressure of from 10 to 50 bar, in particular from 15 to 30 bar, being achieved, which is kept constant for up to 4 h by releasing excess steam. The autoclave is then depressurized to normal pressure at constant temperature in the course of a period of from 0.5 to 3 h. The polymer melt is then discharged from the autoclave, cooled by means of air or nitrogen cooling and then granulated.

The copolyamide thus obtained as a rule has a viscosity number of from 25 to 110 ml/g, preferably of from 30 to 80 ml/g, measured on a 0.5% strength by weight solution in 96% strength sulfuric acid.

To prepare the polyamide dispersions according to the invention, the polyamide granules can be dispersed by intensive stirring in from 30 to 99, preferably from 60 to 90,% by weight, based on the amount of polymer, of water. The preparation of the dispersion customarily takes place at 25° C., but can also be carried out at up to 80° C. After addition of the water, the mixtures are preferably additionally stirred for from 0.5 to 3 h, complete dispersion of the polyamides taking place. The dispersions thus prepared have solids contents of from 1 to 70, preferably of from 10 to 40,% by weight. The light transmission (determined by means of a Vis-spectrometer from Beckmann) is from 50 to 99%, preferably >60%. The particle sizes can be in the range from 40 to 120 mm.

An advantage of the novel sulfonate-bearing polyamides is that they can be processed without problems in water to give dispersions having relatively high solids contents.

Sulfonate-bearing polyamides which contain less than 2.6 mol % of a salt of a sulfonate-bearing dicarboxylic acid can no longer be processed directly to give aqueous dispersions. If the proportion of the sulfonate-bearing monomer is more than 7 mol %, dispersions can indeed be prepared in principle, but due to the high viscosity only up to solids contents of below 10% by weight.

The polyamides according to the invention are thus especially suitable for those hairsetting compositions which are intended to have a particularly low VOC content, ie. are mainly water-based. Preferably, they can be employed in hairsetting compositions having VOC values of <55% by weight. Because of the good self-dispersibility of the polyamides according to the invention, relatively large proportions of organic solvents can be dispensed with.

However, according to the invention suitable film-forming agents in hairsetting compositions are also those sulfonate-containing polyamides which are obtainable by use of lower or higher proportions of sulfonate-bearing monomers, to be precise especially if the hairsetting compositions can have VOC values of >55%. In such a case, the hairsetting compositions are alcoholic or aqueous-alcoholic solutions of the sulfonate-containing polyamides or even solutions of the polyamides in other organic solvents suitable for this purpose. On account of the better evaporability of the organic solvent in comparison to water, these solutions can even be employed as hairsetting compositions having a relatively low solids content, for example in the range from 1 to 10% by weight.

According to the invention, the sulfonate-bearing polyamides can be employed both as the sole film-forming agent in hairsetting compositions and as mixtures with conventional hairsetting polymers. Suitable conventional hairsetting polymers are, for example, anionic polymers such as acrylic acid or methacrylic acid homopolymers or copolymers, copolymers of acrylic acid and acrylamides and copolymers based on alkyl vinyl ethers and monoalkyl maleates, amphoteric polymers such as copolymers of octylacrylamide, acrylate and butylaminoethyl methacrylate as well as nonionic polymers such as vinylpyrrolidone homopolymers, vinylpyrrolidone/vinyl acetate copolymers and copolymers of vinylpyrrolidone, vinyl acetate and vinyl propionate. The ratio of sulfonate-containing polyamides to the conventional hairsetting polymers can be selected corresponding to the desired application properties.

The hairsetting compositions can furthermore contain customary auxiliaries such as, for example, surfactants, emulsifiers or fragrances.

Formulations suitable as hairsetting compositions can, for example, be composed as follows (%=% by weight):

1)
  5% of a polyamide
  0.2% of a mixture of perfume oil and emulsifier in the quantitative ratio 1:3
  10% of ethanol
  84.8% of water 2)
  3.5% of a polyamide
  1.5% of a copolymer of 60% by weight N-vinylpyrrolidone and 40% by weight of vinyl acetate
  0.2% of perfume oil/emulsifier
  94.8% of water Instead of an NVP/VA copolymer, for example, 1.5% of a terpolymer based on acrylate can also be used.

When applying the hairsetting compositions according to the invention, clear, well-drying films are obtained which impart a pleasant sensation to the skin and have good setting action and good washability.

Examples 1 to 6 and Comparison Examples 1 and 2

(Table 1)

2 kg of a monomer mixture of the composition given in Table 1 were initially introduced into a 5 l laboratory autoclave in 1500 ml of water. The autoclave was heated to 280° C. in the course of 1 h, the resulting pressure of about 20 bar being kept constant by releasing excess steam. Pressure and temperature were unchanged for a further hour. The autoclave was then depressurized to normal pressure in the course of 1 h maintaining the temperature of 280° C. Subsequent condensation was then carried out for 2 h in a stream of nitrogen. The melt was then discharged through a nozzle, cooled in an air bed and granulated.

400 g of the granules in each case were dispersed in 600 g of water at room temperature with stirring.

The following tests were carried out on the granules:
  a) Granules before dispersion: determination of the viscosity number (VN) based on DIN 53 246 (0.5% strength solution of the copolyamide in 96% strength $H_2SO_4$).
  b) Determination of the glass transition temperature (Tg) and of the melting range by means of Differential Scanning Calorimetry (DSC 5000 from Mettler) at 20° C./min heating rate.

The characterization of the dispersions was carried out by the following methods:
  a) Determination of the light transmission (LT measurement, 0.01% strength solutions in water, comparison: pure water: LT=100)
  b) Determination of the viscosity in a rotary viscometer (model: RV 20; Haake) at a shear rate of 500 $s^{-1}$; T=23° C.
  c) Determination of the particle size in a nanosizer (model: Autosizer 2C; Malvern)

TABLE 1

Composition and properties according to Examples 1 to 6 (data in mol %)

| Component | Ex. 1 | Ex. 2 | Ex. 3 | Ex. 4 | Ex. 5 | Ex. 6 |
|---|---|---|---|---|---|---|
| A1 ε-Caprolactam | 50 | 60 | 70 | 75 | 60 | 60 |
| A2 1,6-Hexamethylene-diamine | 25 | 20 | 15 | 12.5 | 20 | 20 |
| A3 Sodium 5-sulfoisophthalate | 3 | 3 | 3 | 3 | 5 | 3 |
| A4 Isophthalic acid | 22 | 17 | 12 | 9.5 | 15 | 17 |
| B [%] water | 60 | 60 | 60 | 60 | 70 | 60 |
| VN [ml/g] | 71.5 | 79 | 87 | 112 | 63 | 85 |
| η [mPas] | 98 | 122 | 140 | 110 | 200 | 110 |
| LT [%] | 96 | 99 | 86 | 66 | 100 | 87 |
| Tg [°C.] | 92 | 98 | 69 | 74 | 98 | 59 |
| Particle size [nm] | 77 | 48 | 107 | 140 | 41 | 60 |

EXAMPLES 7 to 12

2 kg of a monomer mixture of the composition given in Table 2 were dissolved in 1500 ml of water and melt-condensed under the conditions shown in Table 2.

TABLE 2

Compositions of the polymers according to Examples 7 to 12 (data in mol %)

| Example No. | 7 | 8 | 9 | 10 | 11 | 12 | 13 | 14 |
|---|---|---|---|---|---|---|---|---|
| ε-Caprolactam | 20 | 20 | 20 | 20 | 20 | 20 | 32 | 50 |
| Adipic acid | — | — | — | — | 34 | 20 | — | — |
| 4,4'-Bis-(diamino-3,3'-dimethyl-cyclohexyl)-methane | 24 | 24 | 24 | 40 | — | — | — | — |
| Hexamethyl-enediamine | 16 | 16 | 16 | — | 40 | 40 | 34 | 25 |
| Sodium 5-sulfoiso-phthalate | 24 | 24 | 12 | 12 | 6 | 20 | 17 | 8 |
| Isophthalic acid | 16 | 16 | 28 | 28 | — | — | 17 | 17 |
| Temperature [°C.] | 270 | 250 | 270 | 270 | 270 | 270 | 270 | 270 |
| Pressure [bar] | 20 | 8 | 20 | 20 | 20 | 20 | 20 | 20 |

Formulation examples

I) 10% by weight of polyamide according to Example 13
   0.4% by weight of a mixture of perfume oil and emulsifier[1]) in the weight ratio 1:3 89.6% by weight of water II) 10% by weight of polyamide according to Example 14 otherwise as in formulation I)

[1]) ethoxylated hydrogenated castor oil, prepared using 40 mol of ethylene oxide

Application Testing

Initial curl droop method

In the initial curl droop method, 2 g of a 15.5 cm long strand of hair are washed twice with Texapon NSO solution (sodium lauryl ether sulfate) having a 10% solids content, then rinsed with water and put into 50% strength ethanol at 40° C. for 15 min. The excess liquid is squeezed out and the hair is wound around a Plexiglas tube (12 mm diameter). It is then dried at from 65 to 70° C. for 1 h. After cooling at room temperature for 15 min, the hair is unwound. The curl is suspended at one end and the curl length ($L_0$) measured. The strand of hair is then sprayed with the hairspray from a distance of about 10 cm for 4 s, the curl being rotated. The curl is then resuspended and put into the climatic chamber. The curl length ($L_t$) is measured at intervals of time. The initial curl droop is given by: $L - L_t / (L - L_0) \times 100$

|  | Formulation I | Formulation II |
|---|---|---|
| Initial curl droop [%] | 79 | 72 |
| Setting | good | good |
| Washability | good | good |

We claim:

1. A process for treating hair, which process comprises applying to the hair an effective amount of an aqueous hairsetting composition prepared by first providing a film-forming agent consisting essentially of a sulfonate-bearing polymer obtained from $A_1$) from 29 to 99 mol % of ε-caprolactam;

$A_2$) from 0.5 to 40 mol % of a diamine having 2 to 18 carbon atoms;

$A_3$) from 0.5 to 25 mol % of a sulfonate-bearing dicarboxylic acid having 4 to 12 carbon atoms; and $A_4$) from 0 to 35 mol % of an additional dicarboxylic acid having 2 to 16 carbon atoms; the mol % in each instance being based on the total amount of components $A_1$) to $A_4$); followed by dispersing the film-forming agent in a member selected from the group consisting of water, an aqueous solution, and an aqueous dispersion.

2. A process of claim 1, wherein the film-forming agent is dispersed in a member selected from the group consisting of water, an aqueous solution, and an aqueous dispersion, in an amount sufficient to provide a solids content from 1 to 70 percent by weight, based on the total weight of the aqueous hairsetting composition.

3. The process of claim 2, wherein the sulfonate-bearing polymer is obtained from $A_1$) from 60 to 80 mol % of ε-caprolactam;

$A_2$) from 5.9 to 35.5 mol % of a diamine having 2 to 18 carbon atoms;

$A_3$) from 2.9 to 6.5 mol % of a sulfonate-bearing dicarboxylic acid having 4 to 12 carbon atoms; and $A_4$) from 3 to 25 mol % of an additional dicarboxylic acid having 2 to 16 carbon atoms.

4. The process of claim 2, wherein the sulfonate-bearing polymer is obtained from $A_1$) from 30 to 94.8 mol % of ε-caprolactam;

$A_2$) from 2.6 to 37 mol % of a diamine having 2 to 18 carbon atoms;

$A_3$) from 2.6 to 7 mol % of a sulfonate-bearing dicarboxylic acid having 4 to 12 carbon atoms; and $A_4$) from 0 to 30 mol % of an additional dicarboxylic acid having 2 to 16 carbon atoms.

5. The process of claim 1, wherein the sulfonate-bearing polymer is obtained from $A_1$) from 30 to 94 mol % of ε-caprolactam;

$A_2$) from 7 to 35 mol % of a diamine having 2 to 18 carbon atoms;

$A_3$) from 2.9 to 6.5 mol % of a sulfonate-bearing dicarboxylic acid having 4 to 12 carbon atoms; and $A_4$) from 3 to 25 mol % of an additional dicarboxylic acid having 2 to 16 carbon atoms.

* * * * *